United States Patent
Kobylinski et al.

[11] 4,022,810
[45] May 10, 1977

[54] METAL CHRYSOTILE METHANE SYNTHESIS CATALYST

[75] Inventors: Thaddeus P. Kobylinski; Harold E. Swift, both of Gibsonia, Pa.

[73] Assignee: Gulf Research & Development Company, Pittsburgh, Pa.

[22] Filed: Feb. 2, 1976

[21] Appl. No.: 654,207

[52] U.S. Cl. .................. 260/449.6 M; 252/457; 252/459
[51] Int. Cl.² .................. C07C 1/04; C07C 1/02
[58] Field of Search ............... 260/449 M, 449.6 M

[56] References Cited

UNITED STATES PATENTS

| | | | |
|---|---|---|---|
| 3,361,535 | 1/1968 | Pollitzer et al. | 260/449 M |
| 3,379,505 | 6/1968 | Holmes et al. | 260/449 M |
| 3,625,664 | 12/1971 | Padovani | 260/449 M |
| 3,625,665 | 12/1971 | Thompson | 260/449 M |
| 3,729,429 | 4/1973 | Robson | 423/328 |
| 3,730,694 | 5/1973 | Wunderlich | 260/449 M |
| 3,912,775 | 10/1975 | Broecker et al. | 260/449.6 M |

OTHER PUBLICATIONS

Moeller et al., Hydrocarbon Processing, Apr. 1974, 69–74.

*Primary Examiner*—Howard T. Mars

[57] ABSTRACT

The conversion of carbon monoxide and hydrogen to produce methane is catalyzed by a layered complex metal silicate composition characterized as having repeating units of the structural formula

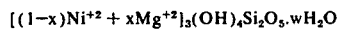

$$[(1-x)Ni^{+2} + xMg^{+2}]_3(OH)_4Si_2O_5 \cdot wH_2O$$

where $x$ is a number from 0.01 to 0.6, this number expressing the atomic fraction of the metals nickel and magnesium and $w$ is a number ranging from 0 to 4.

9 Claims, No Drawings

METAL CHRYSOTILE METHANE SYNTHESIS CATALYST

This invention relates to the conversion of carbon oxides such as carbon monoxide and carbon dioxide and hydrogen to methane using an improved metal chrysotile catalyst. In particular this invention relates to the use of magnesium substituted nickel chrysotile for the conversion of carbon monoxide and hydrogen to methane.

BACKGROUND OF THE INVENTION

The limited supplies of natural gas (methane) in the United States, together with its great usefulness, have provided the necessary incentive for the discovery and development of techniques to produce synthetic natural gas (SNG) by a reaction known as methanation. The methanation reaction generally involves the conversion of synthesis gas to methane and water in the presence of a suitable catalyst. Synthesis gas is a mixture of CO and hydrogen and can be produced by the gasification of coal with steam and oxygen. Suitable catalysts for methanation are described in the prior art and include iron, nickel and ruthenium, among others. The Bureau of Mines Report of Investigation 5137 entitled "Synthesis of Methane" by Murray Greyson et al (July 1955) reports that nickel is superior to iron and that the techniques of catalyst preparation determine to a large extent the process life of the nickel catalyst.

The nickel catalysts investigated by the Bureau and others are typically prepared by precipitating nickel salts such as nickel nitrate onto various supports such as alumina or kieselguhr. In addition to poor aging characteristics, prior art nickel catalysts suffer from their tendency to promote undesired side reactions such as the disproportionation of the CO to $CO_2$ and the formation of carbon either by the decomposition of CO or the formation of higher molecular weight hydrocarbons which eventually deposit and form coke.

The inventors have discovered in accordance with their teachings in copending U.S. Ser. No. 532,848 now U.S. Pat. No. 3,947,483, entitled "Metal Chrysotile Methane Synthesis Catalyst", filed on Dec. 16, 1974, that an improved methanation catalyst comprises a crystalline layered complex metal silicate characterized as having repeating units having the structural formula:

$$[(1-x)Ni^a + xRu^b]_n (OH)_4Si_2O_5 \cdot wH_2O$$

where $x$ is a number from 0 to 1, this number expressing the atomic fraction of the metals nickel and ruthenium, $a$ is the valence of nickel, $b$ is the valence of ruthenium, $n$ is a number equal in value to that defined by the ratio $$6/[a(1-x) + bx]$$

and $w$ is a number ranging from 0 to 4.

It has now been discovered in accordance with the invention that the efficiency of the nickel chrysotile catalysts can be improved together with their thermal stability by the substitution of magnesium for a portion of the nickel in the nickel chrysotile catalysts.

Thus, in accordance with the invention, an improved process has been discovered for the production of methane which comprises contacting a charge stock comprising hydrogen and at least one carbon oxide selected from the group consisting of CO and $CO_2$ wherein the molar ratio of hydrogen to combined carbon oxides is at least 2:1 under methanation conditions with a catalyst comprising a metal silicate characterized as having repeating units having the structrual formula:

$$[(1-x)Ni^{+2} + xMg^{+2}]_3(OH)_4Si_2O_5 \cdot wH_2O$$

where $x$ is a number from 0.01 to 0.6, this number expressing the atomic fraction of the metals nickel and magnesium and $w$ is a number ranging from 0 to 4.

DESCRIPTION OF THE CATALYST

The improved methanation catalyst for use in the process of this invention is a magnesium substituted nickel chrysotile, which is a complex layered metal silicate. These layered complex metal silicates and their methods of preparation are described, for example, in U.S. Pat. No. 3,729,429 to Robson issued Apr. 24, 1973. The specification of the Robson patent is incorporated herein by reference for the purpose of providing a fuller description of the catalyst and a method of preparing the catalyst. It is realized that the materials described by Robson encompass many complex metal silicates while only the magnesium substituted nickel complex metal silicates are claimed in this specification as useful materials to promote the methanation reaction. Robson in his specification describes his metal silicates as useful catalytic agents in hydrocarbon conversion reactions. Illustrative of such reactions are aromatization, isomerization, hydroisomerization, cracking, hydrocracking, polymerization, alkylation, dealkylation, hydrogenation and dehydrogenation, desulfurization, denitrogenation and reforming (see Col. 3, lines 14–18 of the 3,729,429 Robson patent). Nowhere does Robson teach or indicate that his materials, especially the magnesium substituted nickel forms, are useful for the synthesis, as contrasted with the conversion, of hydrocarbons and in particular the synthesis of methane.

More specifically, the catalyst used to promote the desired methanation reaction in accordance with this invention in a crystalline layer complex metal silicate composition characterized as having repeating units having the structural formula $$[(1-x)Ni^{+2} + xMg^{+2}]_3(OH)_4Si_2O_5 \cdot wH_2O$$

where $x$ is a number from 0.01 to 0.6, this number expressing the atomic fraction of the metals nickel and magnesium, and $w$ is a number ranging from 0 to 4.

The preferred metal silicate is where $x$ in the above formula is from 0.05 to 0.4 and most preferably $x$ is 0.09 to 0.25. Should $x$ in the above formula be one, the resulting material would be magnesium chrysotile (asbestos) which has been found to be totally inactive for promoting the methanation reaction. Surprisingly, the substitution of magnesium for a portion of the nickel in the nickel chrysotile improves the yield of methane per gram of nickel in the catalyst. Further, it has been found that the presence of magnesium in the nickel chrysotile improves the thermal stability of the nickel chrysotile and thus an increased catalyst life would be expected. By "thermal stability" is meant the temperature at which the crystal structure undergoes breakdown as evidenced by X-ray diffraction analysis.

The magnesium substituted nickel chrysotile catalysts of this invention are synthetically prepared. One suitable method of preparing the catalysts of this invention is, as noted above, by the technique of Robson in U.S. Pat. No. 3,729,429. In general, this process is to initially synthesize a gel by coprecipitation of the metal oxide or hydroxide with hydrous silica gel in an alkaline medium wherein the pH is above 10, preferably about 12 to 14. For example, the composition of the metal hydroxide layer of the crystal is fixed by selecting the concentration of nickel and magnesium salts to vary the ratio of nickel to magnesium as desired. Any water soluble nickel or magnesium salts, including MgO, can be employed. After the desired gel is produced, it is heated at from about 200° C. to 350° C., preferably 250° C. to 275° C., so that the chrysotile product is crystallized from the synthesis gel with rejection of excess water and soluble salts which are removed by filtration and washing. Other methods will be described later in conjunction with the experimental work. The complex metal silicates as defined above are generally prepared synthetically in hydrated form and are then converted to a dehydrated form by heating prior to use or in situ operation. Since the dehydration reaction is reversible and since water is produced during the methanation reaction, the exact degree of hydration of the catalyst as the reaction proceeds is not known. Thus $w$ in the above formula is defined as ranging from 0 to 4 to indicate that the degree of hydration of the catalyst may vary.

The magnesium substituted nickel chrysotiles are dried to remove surface moisture and may or may not be dehydrated in whole or in part by calcination prior to use. The catalyst also, preferably, undergoes a mild prereduction before use. Calcination is not essential, nor is prereduction with a gas such as hydrogen essential, although varying degrees of calcination and/or prereduction may occur. Since the methanation reaction is operated at elevated temperatures and in the presence of reducing gases, dehydration and reduction of the catalyst will occur during the methanation reaction. Precalcination can suitably occur at temperatures of 300° C. to 500° C. for 2 to 10 hours. Prereduction using a gas such as $H_2$ at flow rates of 50 to 500 cc/min can also suitably occur at temperatures of 300° C. to 500° C. for 2 to 10 hours.

The charge stock for the methanation reaction comprises hydrogen and at least one carbon oxide selected from the group consisting of CO and $CO_2$ wherein the molar ratio of hydrogen to combined carbon oxides is at least 2:1. Preferably the hydrogen to combined carbon oxides molar ratio is from about 3:1 to 4:1, although ratios to 10:1 to 100:1 to 1000:1 or more can be employed.

Ideally the methanation reaction proceeds in accordance with Equation I below when CO is the reactive carbon oxide employed.

EQUATION I $$CO + 3H_2 \rightleftharpoons CH_4 + H_2O$$

Referring to Equation I, stoichiometry indicates that the minimum hydrogen to CO mole ratio is 3:1. Hydrogen to CO ratios as low as 2:1 can be used, as noted above, but reduced reaction efficiency results. Higher hydrogen to CO ratios, e.g. above 3:1, tend to discourage side reactions such as the decomposition of CO to form carbon (coke).

If the hydrogen to CO mole ratio is below about 3:1, a secondary water-gas shift reaction can occur as shown by Equation II below:

EQUATION II $$CO + H_2O \rightleftharpoons CO_2 + H_2$$

Methane and $CO_2$ may also be produced as shown in Equation III below.

EQUATION III $$2CO + 2H_2 \rightleftharpoons CH_4 + CO_2$$

If $CO_2$ is present either initially or via Equations II and III above, methane can also be produced as shown in Equation IV below:

EQUATION IV $$CO_2 + 4H_2 \rightleftharpoons CH_4 = 2H_2O$$

Since hydrogen is the more expensive component of the charge stock, it is naturally preferred to keep the $CO_2$ content of the charge stock as low as possible, albeit a charge consisting essentially of $CO_2$ can be employed if desired. The high molar ratios of $H_2$ to carbon oxides, as noted above, can be used despite the relative high cost of hydrogen, if the methanation reaction (Equations I, III and IV above) is intended as a method of purifying a stream of small concentrations of CO or $CO_2$, e.g. the purification of hydrogen streams destined for ammonia synthesis.

The charge stock for the methanation process of this invention can, of course, be obtained from any suitable source well known to those in the art. For example, if pipeline gas (SNG) is the desired final product, the charge stock for the methanation reaction can be derived from the gasification of coal with steam and oxygen. Initial coal gasification product streams are too low in hydrogen and contain undesirable impurities, especially sulfur compounds which tend to deactivate the catalysts of this invention. A typical coal gasification product on a waterfree basis contains about 29% $CO_2$; 19% CO; 38% $H_2$; 13% methane and small amounts of $H_2S$ and nitrogen. Normally these gases are purified to remove sulfur (to less than 1 ppm) and the gases are then subjected to a water-gas shift reaction (Equation II above) to increase the $H_2$ and thus give a product gas stream which is suitable as a charge stock to a methanation reactor, e.g. where the $H_2$ to combined carbon oxides is at least 2:1, preferbly 3:1 to 4:1.

Diluent gases such as nitrogen or steam can also be present in the charge stock and the amount of inert material in the charge must be balanced by its usefulness as a heat sink versus the reduced space-time yields of products which are achieved because of the presence of the diluent. In one preferred embodiment of the invention, recycle product consisting primarily of methane is used as the diluent heat sink.

The methanation reaction occurs by contacting the charge stock with the desired catalyst under methanation conditions well known in the art. The methanation reaction is highly exothermic and, as noted above, it is preferred to recycle a portion of the product to serve as a heat sink. This can fortunately be done despite the reversibility of Equations I and III above because thermodynamics greatly favor the production of methane.

The charge stock is usually preheated to a temperature of 400° F. to 500° F. (204° C. to 260° C.). This preheated gas is then contacted with the metal chrysotile catalyst of this invention under methanation conditions. By "under methanation conditions" is meant under conditions of temperature, pressure and space velocity for the charge stock whereby the desired methane product is produced by the reaction of $H_2$ and CO and/or $CO_2$. Such methanation conditions are not critical and are well known to those in this art. Typically the temperature of the reaction can be from 374° F. (190° C.), preferably at least 500° F. (260° C.) and can be as high as 900° F. to 1500° F. (482° C. to 816° C.). The gaseous hourly space velocity (GHSV) can suitably be from 1 to 100,000 volumes of gas (total gas including recycle product) per volume of reactor per hour, preferably 100 to 10,000 v/v/hr, and most preferably 500 to 5,000 v/v/hr. The reaction pressure is normally atmospheric to 1000 psi; however, increased pressures of up to 10,000 psi or more can be employed. The effect of pressure on reaction kinetics is limited, but increased pressures do allow for the use of smaller reactors, and the economics of increased pressure versus reactor size must be balanced. An upflow fixed bed operation using extrudates, pellets or other suitably shaped and sized catalyst particles can be employed, but obviously, downflow operation or other types of catalyst beds, e.g. fluid beds, can also be employed.

The product from the reactor differs in composition from the charge stock by an increase in the concentration of methane and water and a decrease in the content of hydrogen and carbon oxides. A portion of the product is suitably recycled for admixture with the preheated charge stock to serve as a heat sink in the reactor. The recycle to feed gas volume ratio is usually about 3:1 but can be from 5:1 to 10:1 or more as desired. Steam can, of course, be used to supplant part or all of the recycle gas.

The invention will be further described with reference to the following experimental work.

EXPERIMENTAL WORK

EXAMPLE 1

(Preparation of synthetic nickel chrysotile)

A synthetic nickel chrysotile was prepared by adding 35 grams of Ludox S.A. (DuPont brand name) colloidal silica with stirring to a solution consisting of 60.1 grams of $NiCl_3.6H_2O$ dissolved in 105 cc's of water. pH electrodes were then immersed into the solution and an initial pH recording was made. A solution of 30 grams of NaOH in 70 cc's of water was then added to the $NiCl_3.6H_2O$ - colloidal silica mixture with stirring, until a final pH of 12 was obtained. The final mixture was stirred for an additional 10 minutes and placed into an autoclave where it was heated under autogenic pressure for 24 hours at 500° F. (260° C.). After cooling, the resulting product, a slurry, was removed from the autoclave, filtered and washed with distilled water until free of NaCl. The precipitate was dried at 250° F. (121° C.) overnight. An X-ray diffraction pattern of the product corresponded to the crystalline compound of the formula $Ni_3OH_4Si_2O_5$ (nickel chrysotile). The amount of nickel in the nickel chrysotile on a weight percent basis was 46.31. The X-ray diffraction pattern is shown on Table I below:

TABLE I

| X-RAY POWDER DIFFRACTION PATTERN | |
|---|---|
| d (A.) | I |
| 7.50 | s. |
| 4.50 | m. |
| 3.67 | s. |
| 2.58 | m. |
| 2.46 | m. |
| 2.10 | w. |
| 1.725 | w. |
| 1.545 | m. |
| 1.320 | w. |
| 1.300 | w. |

The sample was submitted for a surface area measurement by the BET method, and the material was found to have a surface area of about 150 m²/g.

It is to be noted that the preparation of nickel chrysotile followed the procedure of Examples 1–11 in the Robson U.S. Pat. No. 3,729,429 except $NiCl_2$ was used in lieu of $MgCl_2$.

EXAMPLE 2

(Preparation of Magnesium-Nickel Chrysotile Methanation Catalyst)

In this Example, 317.5 g of nickel carbonate and 8.78 g of MgO were mixed together in 2 gallons of water. To this mixture was added 93.6 g of $SiO_2$ (in the form of polysilic acid). The total volume was 6 gallons in a 10-gallon autoclave. This mixture was heated at 300° C. for four hours, which generated at autogeneous pressure of 1240 psig. After the reaction, the autoclave and contents were cooled to room temperature. The resultant slurry was filtered, and the solid was oven-dried at 150° C. for 16 hours. The oven-dried solid was determined to be a magnesium substituted nickel chrysotile having the formula by X-ray diffraction analysis:

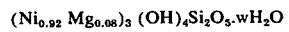

$(Ni_{0.92} Mg_{0.08})_3 (OH)_4 Si_2O_5 \cdot wH_2O$ and having a surface area of 125 m²/g by the BET method.

EXAMPLE 3

Example 2 was repeated, except 303.4 g of nickel carbonate, 18.45 g of MgO and 98.4 g of $SiO_2$ were employed. The catalyst was determined to have the following formula by X-ray diffraction analysis:

$(Ni_{0.83}Mg_{0.16})_3(OH)_4Si_2O_5 \cdot wH_2O$ and having a surface area of 110 m²/g by the BET method.

EXAMPLE 4

In the run for this Example, a magnesium substituted nickel chrysotile was prepared by using the following solutions and procedure:

| | |
|---|---|
| Solution A: | 35 g Ludox S.A. (DuPont Brand) colloidal silica; |
| Solution B: | 50.08 g $NiCl_2 \cdot 6H_2O$ in 100 cc distilled water and 9 g $MgO_2 \cdot 6H_2O$; |
| Solution C: | 33 g of NaOH dissolved in 75 cc of water. |

Solution A was added to B with stirring, and pH was measured; then solution C was added with stirring until pH = 12 was obtained. After 10 minutes of stirring at pH 12, the solution was placed in the autoclave and heated under autogenic pressure at 260° C. for 28 hours. After filtering and washing free of NaCl, the precipitate was dried at 120° C. for 18 hours. An X-ray diffraction corresponded to the crystalline compound having the formula:

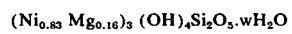

$(Ni_{0.83}Mg_{0.16})_3(OH)_4Si_2O_5 \cdot wH_2O$

The surface area was determined to be 147 m²/g by the BET method.

The feedstock for use in all of the experimental work to be described below consisted of 5.6 mole percent CO; 21.0 mole percent hydrogen; and 73.4 mole percent methane. The function of the methane was to serve as a heat sink. The composition of this charge stock was chosen to simulate charge stocks which are used in commercial methanation units.

A first series of runs were made using the catalyst of Example 2 above. The feedstock was passed through the catalyst bed in all of the runs in this first series at a gaseous hourly space velocity of 4000 volume of feedstock per volume of catalyst per hour. The purpose of the first series of runs was to determine the activity of the catalyst of Example 2 by varying temperatures from 190° C. through 300° C. The results of the runs are shown on Table II below.

TABLE II

| Ex. No. | Catalyst Bed Temperature ° C | Exit Gas Composition Mole% | | | % CO Conversion |
|---|---|---|---|---|---|
| | | CO | H₂ | CH₄ | |
| 5 | 190 | 5.3 | 20.0 | 74.7 | 5.4 |
| 6 | 200 | 5.0 | 19.0 | 76.0 | 10.7 |
| 7 | 220 | 4.1 | 16.2 | 79.7 | 26.8 |
| 8 | 260 | 1.4 | 8.3 | 90.4 | 75.0 |
| 9 | 300 | 0.0 | 4.2 | 95.8 | 100.0 |

The selectivity in all of the runs in Table II to methane was 100 percent; that is, no $CO_2$ was produced. Negligible or at least unmeasurable amounts of carbon were produced in the runs. Referring to Table II, it can be seen that as the temperature is increased, the percent CO conversion also increases so that at 300° C. the percent CO conversion is 100 percent. Overall the results in Table II illustrate the magnesium substituted nickel chrysotile catalyst is an active catalyst for the methanation reaction.

A second series of runs was made, similar to the first series except the catalyst of Example 3 was employed in place of the catalyst from Example 2. The results of these runs are shown in Table III below.

TABLE III

| Ex. No. | Catalyst Temperature ° C. | Exit Gas Composition Mole % | | | % CO Conversion |
|---|---|---|---|---|---|
| | | CO | H₂ | CH₄ | |
| 10 | 195 | 5.1 | 19.4 | 75.5 | 8.9 |
| 11 | 260 | 1.0 | 7.0 | 92.0 | 82.1 |
| 12 | 290 | 0.0 | 4.1 | 95.9 | 100.0 |

The selectivity in all of the Examples in Table III to methane was again 100 percent. The runs in Table III again illustrate that substantially complete conversion of CO occurs at a temperature of about 290° C., illustrating again that the magnesium substituted nickel chrysotile catalysts of this invention are active for the methanation reaction.

A third series of experiments was run similar to those in the first series of runs, except the catalyst of Example 4 was employed along with a constant temperature of 304° C. at varying gaseous hourly space velocities to determine the effect of an increased space velocity (decreased reaction time) on the percent CO conversion. The results of this third series of runs are shown in Table IV below.

TABLE IV

| Ex. No. | GHSV of the Feed | Exit Gas Composition Mole% | | | % CO Conversion |
|---|---|---|---|---|---|
| | | CO | H₂ | CH₄ | |
| 13 | 5,000 | 0 | 4.1 | 95.9 | 100 |
| 14 | 20,000 | 0.8 | 6.6 | 92.6 | 85 |
| 15 | 50,000 | 3.4 | 14.4 | 82.2 | 39 |
| 16 | 100,000 | 4.3 | 17.1 | 78.6 | 22 |
| 17 | 150,000 | 5.0 | 19.2 | 75.8 | 9 |

Referring to Table IV, it can be seen that as the GHSV increases from 5,000 to 20,000, the percent CO conversion decreases from 100 to 85 (compare Examples 13 and 14). Further increases in GHSV, as shown in Examples 15, 16 and 17, result in further decreases in CO conversion.

A fourth series of runs was made, again similar to the first series, except chrysotile catalysts having various amounts of magnesium and nickel were employed, and the gaseous hourly space velocity was constant at 5,000. Runs were made at 190° C., 240° C., and 275° C. for the purpose of determining the methane yield per gram of nickel in the catalyst as an element. The results are shown in Table V below:

TABLE V

| Ex. No. | Molar Ratio of Mg/Ni | CH₄ Yield[a] per Gram of Ni (as an element) at temperature ° C. | | |
|---|---|---|---|---|
| | | 190 | 240 | 275 |
| 18 | 0/1[b] | 4.0 | 30.6 | 88.0 |
| 19 | 1/11[c] | 4.7 | 34.0 | 90.0 |
| 20 | 1/5[d] | 5.3 | 37.8 | 100.0 |
| 21 | 1/0[e] | 0 | 0 | 0 |

[a] Moles CH₄ from 100 moles of CO in feed.
[b] Chrysotile of the formula Ni₃(OH)₄Si₂O₅ made as per Ex. 1.
[c] Chrysotile of the formula Ni₂.₇₅Mg₀.₂₅(OH)₄Si₂O₅ catalyst of Example 2)
[d] Chrysotile of the formula Ni₂.₅Mg₀.₅(OH)₄Si₂O₅ catalyst of Example 4)
[e] Mg chrysotile.

Referring to Table V, it can be seen from Example 21 that magnesium chrysotile is a totally inactive catalyst for the methanation reaction at temperatures of 190° to 275° C. Nickel chrysotile as shown by Example 18 results in a yield of methane per gram of nickel of 88 moles of methane per 100 moles of CO in the feed at a temperature of 275° C. Surprisingly, as magnesium is substituted for a portion of the nickel in the catalyst, as shown by Examples 19 and 20, an increase in the yield of methane to 90 and 100 percent, respectively, occurs despite the fact that magnesium chrysotile is totally inactive as shown by Example 21. The figures of methane yield per gram of nickel as shown in Table V were calculated by measuring the moles of methane produced per 100 moles of CO in the feed and dividing this figure by the grams of nickel in the particular catalyst.

Additional work was done to illustrate the thermal stability of the nickel chrysotile and magnesium substituted nickel chrysotile catalysts. These data are shown in Table VI below.

TABLE VI

Intensity of the Strongest X-Ray Diffraction Line[a] of Ni Chrysotile and Mg-Ni Chrysotile Samples as a Function of Calcination Temperature

| Ex. No. | | Calcination Temp: °C | | |
|---|---|---|---|---|
| | | 400[b] | 450[b] | 500[b] |
| 22 | $Ni_3(OH)_4Si_2O_5 \cdot wH_2O$ | 59 | 10 | 0 |
| 23 | $(Ni_{0.92}Mg_{0.08})_3(OH)_4Si_2O_5 \cdot wH_2O$ | 62 | 39 | 5 |
| 24 | $(Ni_{0.83}Mg_{0.16})_3(OH)_4Si_2O_5 \cdot wH_2O$ | 66 | 27 | 3 |

[a] Line corresponds to a lattice spacing of 7.5 A occurring at 11.8° (2θ) with CuK$_\alpha$ radiation.
[b] Samples calcined for 10 hours at each temperature; separate and new samples were used at each temperature.

Referring to Table VI above, it can be seen that the addition of Mg increases the intensity of the line at any given calcination temperature showing an increased thermal stability for the Mg-Ni chrysotiles.

Resort may be had to such variations and modifications as fall within the spirit of the invention and the scope of the appended claims.

We claim:

1. A process for the production of methane which comprises:
contacting a charge stock comprising hydrogen and at least one carbon oxide selected from the group consisting of CO and $CO_2$ wherein the molar ratio of hydrogen to combined carbon oxides is at least 2:1 under methanation conditions with a catalyst comprising a metal silicate characterized as having repeating units having the structural formula:

$$[(1-x)Ni^{+2} + xMg^{+2}]_3(OH_4)Si_2O_5 \cdot wH_2O$$

where $x$ is a number from 0.01 to 0.6, this number expressing the atomic fraction of the metals nickel and magnesium, and $w$ is a number ranging from 0 to 4.

2. A process in accordance with claim 1 wherein the value of $x$ in the formula is 0.05 to 0.4.

3. A process in accordance with claim 2 wherein the molar ratio of hydrogen to combined carbon oxides in the charge stock is from 2:1 to 4:1.

4. A process in accordance with claim 1 wherein the value of $x$ is 0.09 to 0.25; the molar ratio of hydrogen to combined carbon oxides in the charge stock is from 2:1 to 4:1; and the methanation conditions include a temperature from 190° C. to 816° C. and a gaseous hourly space velocity from 1 to 100,000.

5. A process according to claim 4 wherein the molar ratio of hydrogen to combined carbon oxides is about 3:1.

6. A process according to claim 5 wherein the charge stock is derived from the gasification of coal.

7. A process in accordance with claim 4 wherein the methanation conditions include a temperature from 260° C. to 482° C.

8. A process for the production of methane which comprises:
contacting a charge stock consisting of CO, hydrogen, and methane wherein the molar ratio of hydrogen to CO is at least 2:1 under methanation conditions with a catalyst having improved thermal stability comprising a metal silicate characterized as having repeating units having the structural formula:

$$[(1-x)Ni^{+2} + xMg^{+2}]_3(OH_4)Si_2O_5 \cdot wH_2O$$

where $x$ is a number from 0.01 to 0.6, this number expressing the atomic fraction of the metals nickel and magnesium, and $w$ is a number ranging from 0 to 4.

9. A process in accordance with claim 8 wherein the temperature is 275° C. to result in substantially complete conversion of the CO to methane.

* * * * *